US008846344B2

(12) United States Patent
Goletz et al.

(10) Patent No.: US 8,846,344 B2
(45) Date of Patent: Sep. 30, 2014

(54) PROCESS FOR THE PURIFICATION OF GLYCOPROTEINS

(75) Inventors: Steffen Goletz, Berlin (DE); Lars Stockl, Berlin (DE)

(73) Assignee: Glycotope GmbH, Berlin (DE)

( * ) Notice: Subject to any disclaimer, the term of this patent is extended or adjusted under 35 U.S.C. 154(b) by 0 days.

(21) Appl. No.: 13/511,285

(22) PCT Filed: Nov. 24, 2010

(86) PCT No.: PCT/EP2010/007115
§ 371 (c)(1),
(2), (4) Date: May 22, 2012

(87) PCT Pub. No.: WO2011/063943
PCT Pub. Date: Jun. 3, 2011

(65) Prior Publication Data
US 2012/0252069 A1    Oct. 4, 2012

Related U.S. Application Data

(60) Provisional application No. 61/263,931, filed on Nov. 24, 2009.

(30) Foreign Application Priority Data

Nov. 24, 2009   (EP) .................................... 09014585

(51) Int. Cl.
*A61K 38/00* (2006.01)
*C07K 14/59* (2006.01)
*A61K 38/24* (2006.01)
*C07K 1/22* (2006.01)
*C07K 1/18* (2006.01)
*C07K 1/36* (2006.01)

(52) U.S. Cl.
CPC .. *C07K 1/36* (2013.01); *C07K 14/59* (2013.01)
USPC ........... 435/69.4; 530/398; 530/412; 530/416

(58) Field of Classification Search
None
See application file for complete search history.

(56) References Cited

U.S. PATENT DOCUMENTS

2006/0026719 A1    2/2006  Kieliszewski et al.
2011/0152506 A1*   6/2011  Wienand et al. .............. 530/397

FOREIGN PATENT DOCUMENTS

| EP | 0276551 A1 | 8/1988 | |
|----|------------|--------|---|
| EP | 0505500 B1 | 9/1992 | |
| WO | 96/32413 A1 | 10/1996 | |
| WO | 01/85296 A1 | 11/2001 | |
| WO | 2005/110015 A2 | 11/2005 | |
| WO | WO 2006/051070 | * 11/2005 | ............ A61K 38/04 |
| WO | 2006/051070 | 5/2006 | |

OTHER PUBLICATIONS

Rohr, JS and Avadalovic, N "Separation of Human Serum Transferrin Isoforms by High-Performance Pellicular Anion-Exchange Chromatography" Protein Expression and Purification (1996) 7 39-44.*
Kurnik, R et al. "Buffer Exchange Using Size Exclusion Chromatography, Countercurrent Dialysis, and Tengential Flow Filtration: Models, Development and Industrial Application" Biotechnology and Bioengineering (1995) 45 149-157.*
Brorson, K et al. "Bracketed Generic Inactivation of Rodent retroviruses by Low pH Treatment for Monoclonal Antibodies and Recombinant Proteins" Biotechnology and Bioengineering (2003) 82 321-329.*
Kalbfuss, B. et al. "Purification of Cell Cultured Dervied Human Influenza A Virus by Size Exclusion and Anipn Exchange Chromatography" Biotechnology and Bioengineering (2007) 96 932-944.*
Knauf, M. et al "Relationship of Effective Molecular Size to Systemic Clearance in Rats of Recombinant Interleukin-2 Chemically mModified with Water-soluble Polymers" The Journal of Biological Chemistry (1988) 263, 15064-15070.*
Olijve, W. et al. "Molecular biology and biochemistry of human recombinant follicle stimulating hormone" Molecular Human Reproduction (1996) 2 371-382.*
Bousfield et al. "Chromatofocusing fail to seperate hFSH isoforms on the basis of glycan structure" 2008 Biochemistry 47, 1708-1720.*
El Rassi, Ziad, "Recent Progress in reversed-phase and hydrophobic interaction chromatography of carbohydrate species," Journal of Chromatography A, vol. 720:93-118 (1996).
Funderburgh, James L et al., "Arterial Lumican, Properties of a Corneal-Type Keratan Sulfate Proteoglycan from Bovine Aorta," The Journal of Biological Chemistry, vol. 266(36):24773-24777 (1991).
International Search Report for Application No. PCT/EP2010/007115, 3 pages, dated Jan. 5, 2011.
International Preliminary Report on Patentability and Written Opinion for Application No. PCT/EP2010/007115, 6 pages, dated May 30, 2011.
Clark-Lewis, Ian et al., "Purification to Apparent Homogeneity of a Factor Stimulating the Growth of Multiple Lineages of Hemopoietic Cells," The Journal of Biological Chemistry, vol. 259(12):7488-7494 (1984).
De Cristofaro, Raimondo et al., "Human platelet glycocalicin purification by phenyl boronate affinity chromatography coupled in anion-exchange high-performance liquid chromatography," Journal of Chromatography, vol. 426:376-380 (1988).
Erbayraktar, Serhat et al., "Asialoerythropoietin is a nonerythropoietic cytokine with broad neuroprotective activity in vivo," PNAS, vol. 100(11):6741-6746 (2003).

(Continued)

*Primary Examiner* — Suzanne M Noakes
*Assistant Examiner* — Gerard Lacourciere
(74) *Attorney, Agent, or Firm* — Nelson Mullins Riley & Scarborough LLP; Jane E. Remillard, Esq.; Jill Gorny Sloper, Esq.

(57) ABSTRACT

The present invention relates to a process for the purification of a glycoprotein comprising subjecting a liquid containing said glycoprotein to the steps of: a) reverse phase chromatography, b) size exclusion chromatography, and c) hydrophobic interaction chromatography. Also provided is a manufacturing process for producing a glycoprotein of interest.

23 Claims, No Drawings

(56) References Cited

OTHER PUBLICATIONS

Liu, Xiao-Chuan et al., "Studies on Oriented and Reversible Immobilization of Glycoprotein using Novel Boronate Affinity Gel," Journal of Molecular Recognition, vol. 9:462-467 (1996).

International Preliminary Report on Patentability and Written Opinion for Application No. PCT/EP2011/000302, 6 pages, dated Jul. 31, 2012.

Zhe, Yan, et al., "Heterogeneity and Chromatographic Purification of Glycoprotein Hormones," Progress in Chemistry, vol. 19(2) (Dec. 31, 1999).

* cited by examiner

PROCESS FOR THE PURIFICATION OF GLYCOPROTEINS

The present invention relates to a process for the purification of glycoproteins, such as FSH (follicle stimulating hormone), LH (luteinizing hormone), CG (chorionic gonatropin) and TSH (thyroid-stimulating hormone) and to the manufacturing of a recombinant glycoprotein of interest employing a respective purification process.

Glycoproteins, are proteins that contain oligosaccharide chains covalently attached to polypeptide side-chains. Glycoproteins can have a vast number of different biological functions including structural, protective, carrier, hormone or enzyme functions. Accordingly various glycoproteins can be used as pharmaceuticals. The provision of such glycoproteins is thus highly desirable. Several glycoproteins can nowadays be produced recombinantly, which however requires extensive purification procedures to extract the targeted glycoprotein from the cell culture harvest.

An important class of glycoproteins are gonatropins, a family of four closely related hormones, which includes FSH, LH, CG and TSH (Glycobiology, vol. 13, no. 3, pages 179-189, 2003). FSH is used for instance in the treatment of infertility and reproductive disorders in both female and male patients. Also hCG and LH are used in fertility treatment, alone or in combination with FSH.

In nature, FSH is produced by the pituitary gland. For pharmaceutical use, FSH may be produced recombinantly (rFSH), or it may be isolated from the urine of postmenopausal females (uFSH).

FSH is used in female patients in ovulation induction (OI) and in controlled ovarian hyperstimulation (COH) for assisted reproductive technologies (ART). In a typical treatment regimen for ovulation induction, a patient is administered daily injections of FSH or a variant (about 75 to 300 IU FSH/day) for a period of from about 6 to about 12 days. In a typical treatment regimen for controlled ovarian hyperstimulation, a patient is administered daily injections of FSH or a variant (about 150-600 IU FSH/day, but also as low as 75 IU FSH/day) for a period of from about 6 to about 12 days.

FSH is also used to induce spermatogenesis in men suffering from oligospermia. A regimen using 150 IU FSH 3 times weekly in combination with 2,500 IU hCG twice weekly has been successful in achieving an improvement in sperm count in men suffering from hypogonadotrophic hypogonadism (Burgues et al.; Subcutaneous self-administration of highly purified follicle stimulating hormone and human chorionic gonadotrophin for the treatment of male hypogonadotrophic hypogonadism. Spanish Collaborative Group on Male Hypogonadotrophic Hypogonadism; Hum. Reprod.; 1997, 12, 980-6).

Because of the importance of FSH in the treatment of fertility disorders, the provision of FSH of high purity and high specific activity is desirable. FSH treatment requires repeated injections. Highly purified FSH preparations can be administered subcutaneously, permitting self-administration by the patient, thus increasing patient convenience and compliance.

Lynch et al. (The extraction and purification of human pituitary follicle-stimulating hormone and luteinising hormone; Acta Endocrinologica, 1988, 288, 12-19) describe a method for purifying human pituitary FSH. The method involves anion and cation exchange chromatography, immunoaffinity extraction and size exclusion chromatography.

WO 98/20039 (IBSA Institut Biochimique SA) describes a process for the purification of human urinary FSH starting with urinary extracts called human menopausal gonadotrophins (hMG). The process uses ion-exchange chromatography on weakly basic anionic exchange resins of the DE[Xi]AE type followed by affinity chromatography on resin having an anthraquinone derivative as a ligand.

WO 00/63248 (Instituto Massone SA) describes a process for the purification of gonadotrophins, including FSH, from human urine. The process involves the following steps: ion exchange chromatography with a strong cationic resin of the type sulphopropyl, ion exchange chromatography with a strong anionic resin, and hydrophobic interaction chromatography (HIC).

Chiba et al. [Isolation and partial characterisation of LH, FSH and TSH from canine pituitary gland; Endocrinol. J., 1997, 44, 205-218] describe a technique for purifying canine pituitary gonadotrophins, including FSH, using Concanavalin (Con) A affinity chromatography, hydrophobic interaction chromatography (HIC) and immobilized metal ion chromatography with $Cu^{++}$.

WO 88/10270 (Instituto di Ricerca Cesare Serono SPA) describes a method for purifying human FSH from urine. The process involves immunochromatography with FSH-specific immobilized monoclonal antibodies bound to Sepharose 4B by divinyl sulphone, followed by reverse phase HPLC.

EP 1 106 623 A1 discloses a method for purifying FSH from biological samples for example from human pituitary glands or human postmenopausal urine by use of dye affinity chromatography.

Processes for the purification of recombinant FSH are disclosed in WO 2005/063811 A1, WO 2006/051070 A1, WO 2007/065918 A2 and WO 2009/000913 A1.

WO 2009/000913 A1 discloses an FSH producing cell clone, a method of producing FSH using the cell clone and purifying the obtained recombinant FSH from the cell culture supernatant. The purification may be performed by one or more steps known to the expert, including ion exchange chromatography, hydrophobic interaction chromatography, hydroxyapatite chromatography, affinity chromatography and gel filtration.

WO 2005/063811 A1 discloses a method for purification of recombinant FSH using the steps (1) ion exchange chromatography, (2) immobilised metal ion chromatography, and (3) hydrophobic interaction chromatography.

WO 2006/051070 A1 discloses a method for purification of recombinant FSH using the steps (1) dye affinity chromatography, (2) hydrophobic interaction chromatography, and (3) reverse phase chromatography, which may be carried out in any order.

WO 2007/065918 A2 discloses a method for purification of recombinant FSH using the steps (1) dye affinity chromatography, (2) weak anion exchange chromatography, (3) hydrophobic interaction chromatography, and (4) strong anion exchange chromatography, which may be carried out in any order.

The object of the present invention therefore is to provide a preferably cost-efficient purification process which renders glycoproteins such as FSH in high yield and purity.

Accordingly the present invention relates to a purification process for glycoproteins such as FSH comprising subjecting a liquid containing the glycoprotein to the following steps:
 a) reverse phase chromatography (RPC);
 b) size exclusion chromatography (SEC); and
 c) hydrophobic interaction chromatography (HIC).

The steps a), b) and c) may be carried out in any order. It is preferred that reverse phase chromatography or hydrophobic interaction chromatography is performed as the first of the three chromatography steps. In a more preferred embodiment reverse phase chromatography is performed as the first of the three chromatography steps.

The purification process may optionally comprise additional steps, e.g. ion exchange chromatography such as anion exchange chromatography or cation exchange chromatography, affinity chromatography such as dye affinity chromatography, immune affinity chromatography, lectin affinity chromatography or perborate affinity chromatography, filtration such as diafiltration, ultrafiltration or nanofiltration, and/or at least one virus inactivation step. In a preferred embodiment the process of the present invention includes an anion exchange chromatography (AEX) as a fourth chromatography step.

In a preferred embodiment the steps (a), (b) and (c) are performed in the sequence of
   (1) reverse phase chromatography,
   (2) size exclusion chromatography, and
   (3) hydrophobic interaction chromatography.

Performing RPC as first chromatography step is preferred because this embodiment provides the option to load rather "raw" biological liquids such as crude glycoprotein, natural source liquids, cell culture medium or cell lysates directly onto the RPC, optionally after a clearing (e.g. filtration), concentration and/or buffer exchange step as described below. This embodiment provides the advantage that even when using such sample liquids high amounts of the sample can be loaded onto the chromatography column without the danger of clogging or overloading the column. Furthermore, the buffer conditions required for RPC do not lead to excessive aggregation of components of the sample solution. In summary, using RPC as first chromatography step reduces the number of preparation steps which are necessary before starting the chromatographic purification and allows the use of high amounts of sample solution with high amounts of other components besides the glycoprotein of interest.

In another preferred embodiment an anion exchange chromatography (d) is performed subsequent to size exclusion chromatography (2) and prior to hydrophobic interaction chromatography (3). As described above, additional steps may be performed in addition to and also between the steps.

The purification method of the invention provides the glycoprotein such as FSH in high purity, which may then be formulated as a pharmaceutical composition. The purity in general is above 90%, preferably >95% w/w, more preferably >99% w/w, even more preferably >99.5% w/w, based on total protein. Furthermore, the purification method of the invention is easily scalable, even up to industrial size, without major changes in the purification conditions.

The crude glycoprotein which forms the starting material for the purification process according to the present invention may be provided in or obtained from liquids of natural sources or by recombinant techniques such as e.g. in cell culture harvests containing the glycoprotein. Typically, the starting material as obtained from a natural source or a cell harvest, preferably from a cell harvest, is clarified first (e.g. by filtration) and then optionally concentrated (e.g. by using ultrafiltration) and/or buffer exchanged (e.g. through a diafiltration step) prior to being captured by the first chromatographic step.

In the steps of chromatography typically commercially available resins are used, preferably polymer-based resins or agarose-based resins. It is also possible to use membrane chromatography in which the resin is replaced by a functionalised membrane such as SARTOBIND membranes (Sartorius) or CHROMASORB (Millipore).

The steps of the purification process of the present invention are outlined in the following in more detail.

Reverse Phase Chromatography Step (a)

The process involves a step of reverse phase chromatography (a). In a preferred embodiment, especially in the case of recombinant glycoproteins, the reverse phase chromatography is used as capture step in which the glycoprotein is enriched, e.g., from the natural source liquid or the cell culture harvest. It is preferred to perform a virus inactivation subsequent to elution from the RPC column.

"Reverse phase chromatography" according to the invention in particular refers to a chromatography step wherein a non-polar stationary phase and preferably a polar mobile phase are used. In reverse phase chromatography, normally polar compounds are eluted first while non-polar compounds are retained.

The reverse phase chromatography is usually performed by equilibrating and loading the column, followed by a wash and subsequent elution, each with a buffer preferably containing an organic solvent such as acetonitrile or isopropanol. The organic solvent such as isopropanol can be used for virus inactivation subsequent to elution.

The equilibration, load, wash and elution is preferably carried out by using a mobile phase buffering at mildly alkaline pH, for example at or about pH 7 to 8.5, more preferably at or about 7.5. In a preferred embodiment, the buffering species is a phosphate buffer, preferably sodium phosphate. Alternate buffers adequate for a pH at or around 7.5 include BES, MOPS, ammonium acetate, TES, HEPES.

It is preferred that no buffer exchange is performed after step (a) in case that subsequently step (b) (SEC) is performed. The buffer exchange can be achieved then by the subsequent SEC by using as running buffer the preferred buffer for the next chromatography step such as the AEX or HIC chromatography.

In a preferred embodiment the buffer solutions used for the RPC step contain an organic solvent, the concentration of which is modulated for different phases of the chromatography step (equilibration, load, wash and elution). Preferably the organic solvent is a water miscible organic solvent such as acetonitrile or an alcohol (such as methanol, ethanol, etc.), more preferably isopropanol.

In the equilibrating and loading buffer solution and in the wash buffer solution the organic solvent is preferably contained in an amount between 5 and 15% v/v of total buffer solution, preferably between 5 and 12% v/v of total buffer solution. The wash buffer is typically identical to the loading buffer. In the elution buffer solution the organic solvent is preferably contained in a higher amount than in the loading buffer, preferably in an amount between 15 and 22% v/v of total buffer solution, more preferably between 16 and 20% v/v of total buffer solution.

In preferred embodiments, the reverse phase chromatography step can include a virus inactivation step. Virus inactivation may be achieved by incubating the protein loaded onto, bound to or eluted from the column in the presence of an organic solvent, preferably isopropanol or ethanol. The incubation time and incubation temperature preferably are chosen so as to effect a desired degree of virus inactivation and in particular depend on the concentration and nature of the organic solvent used. Furthermore, these parameters should also be adjusted depending on the stability of the glycoprotein to be purified. For example, the protein is incubated for at least 15 min, preferably for at least 30 min, at least 45 min, at least 1 h, at least 2 h, at least 3 h or at least 6 h. The incubation can be performed at low temperature such as at or below 4° C. or at or below 10° C., or it can be performed at about room temperature. The incubation can be performed directly after the sample has been loaded onto the column, during or after the washing step, after applying the elution buffer but prior to elution of the glycoprotein, or after elution of the glycoprotein. If isopropanol is used as the organic solvent, virus inactivation is preferably done at an isopropanol concentration of at least 15% (v/v), preferably at about 18% (v/v). In this case, the glycoprotein is preferably incubated for about 2 h, preferably at room temperature. Preferably, the virus inactivation is performed after elution of the glycoprotein from the reverse phase chromatography column, preferably in the elution buffer used. However, optionally further components may be added to the glycoprotein solution after elution from the column, in particular for enhancing the virus inactivation and/or the glycoprotein stability. Using a virus inactivation step during the RPC, the process of the invention may be performed without any further virus inactivation step. However, various virus inactivation steps may also be combined, for example a virus inactivation during RPC and a virus inactivation via nanofiltration and/or via pH adjustment as described herein.

In a particularly preferred embodiment, the product-contacting buffers for the step of RPC (equilibration, load, wash, elution) contain an antioxidant, such as L-methionine. Alternate antioxidants include t-butyl-4-methoxyphenol, 2,6-bis (1,1-dimethylethyl)-4-methyl phenol; potassium or sodium bimetabisulfite, sodium bisulfite.

Reversed phase column material is made of a resin to which a hydrophobic material may be attached. Typical column materials are silica and polystyrene; hydrophobic ligands may optionally be attached. In case of substituted resins, the resin is substituted with a hydrophobic ligand, typically selected from (but not limited to) aliphates, such as $C_2$, $C_4$, $C_6$, $C_8$, $C_{10}$, $C_{12}$, $C_{14}$, $C_{16}$, or $C_{18}$ or derivates of these, e.g. cyanopropyl (CN-propyl), or branched aliphates, or benzene-based aromates, such as phenyl, or other polar or nonpolar ligands. The ligand may be a mixture of two or more of these ligands. Suitable polystyrene based resins include, without limitation, resins supplied by Rohm Haas (e.g. Amberlite XAD or Amberchrom CG), Polymer Labs (e.g. PLRP-S), GE Healthcare (e.g. Source RPC), Applied Biosystems (e.g. Poros R). A particularly preferred resin is Source 30 RPC (GE Healthcare).

The manufacturing processes for and optimal features of the column material often require that a linking group also called a spacer is inserted between the resin and the ligand. Other parameters in the methods of the present invention include load, i.e. amount of protein which is loaded to the column and flow rate. These parameters may be optimised through experiments which are known to the person skilled in the art.

The glycoprotein is typically loaded onto the column in a concentration of at least about 0.1 mg per ml of resin, such as, e.g., at least about 0.2 mg, 0.5 mg, 1 mg, 2 mg, 5 mg, 10, or 20 mg per ml of resin; or in the range of 0.1-200 mg, such as, e.g., 0.1-100 mg, 0.5-100 mg, 1-50 mg, or 2-30 mg per mL of resin; preferably the load is at least 1 mg per mL resin. Measurement of packed resin volume is typically done in suspension or similar mode.

Size Exclusion Chromatography Step (b)

The process of the present invention also involves a step of size exclusion chromatography (b), e.g. for further purifying and/or re-buffering of the glycoprotein. The size exclusion chromatography comprises the step of equilibrating and loading the eluate of the previous chromatography step to a gel filtration matrix equilibrated with a buffer having a composition which is desired for storage or further processing of the glycoprotein at a pH of typically between 6.5 and 9, preferably about 8.5.

For performing size exclusion chromatography, the gel is typically selected from the groups of polymeric gels including, but not limited to dextra-based gels such as SEPHADEX (e.g. SEPHADEX G-25) or polyacrylamide gels such as SEPHACRYL (e.g. SEPHACRYL-S400), agarose-based gels such as SUPEROSE or SEPHAROSE (e.g. SEPHAROSE CL-4B), and composite gels prepared from two kinds of gels such as SUPERDEX 200 combining DEXTRAN (SEPHADEX) and crosslinked Agarose (SUPEROSE) gels.

In a preferred embodiment the buffer is selected from the group consisting sodium phosphate, ammonium acetate, MES (2-(N-morpholino)ethanesulfonic acid), Bis-Tris (2-bis (2-hydroxyethyl)amino-2-(hydroxymethyl)-1,3-propanediol), ADA (N-(2-Acetamido) iminodiacetic acid), PIPES (piperazine-N,N'-bis(2-ethanesulfonic acid), ACES (N-(2-Acetamido)-2-aminoethanesulfonic acid), BES (N,N-Bis(2-hydroxyethyl)-2-aminoethane-sulfonic acid), MOPS (3-(N-morpholino) propanesulfonic acid), TES (N-Tris(hydroxymethyl)methyl-2-aminoethanesulfonic acid), HEPES (N-2-Hydroxyethyl-piperazine-N'-2-ethanesulfonic acid), preferably sodium phosphate or ammonium acetate, more preferably ammonium acetate.

Optionally said buffer comprises in addition an inorganic salt, preferably a halide of an alkaline metal, more preferably potassium chloride or sodium chloride, most preferably sodium chloride, wherein the concentration of said inorganic salt is about 0 to 500 mM, preferably 0 to 300 mM, most preferably about 0 to 50 mM. In a preferred embodiment the buffer is salt free.

In a particularly preferred embodiment, the product-contacting buffers for the step (b) of SEC (equilibration, load, elution) contain an antioxidant, such as L-methionine. Alternative antioxidants include t-butyl-4-methoxyphenol, 2,6-bis (1,1-dimethylethyl)-4-methyl phenol; potassium or sodium bimetabisulfite, sodium bisulfite.

The size exclusion chromatography further comprises the step of eluting the glycoprotein from said gel filtration matrix by isocratic elution, i.e. the elution buffer has about the same, preferably the same composition as the buffer used for equilibration and/or loading. The flow through may be recorded by UV absorption at 280 nm and the fraction containing the glycoprotein is collected.

Hydrophobic Interaction Chromatography Step (c)

The process of the present invention also involves a step of hydrophobic interaction chromatography (c). Hydrophobic interaction chromatography is usually performed by equilibrating and loading the column, followed by a wash and subsequent elution.

Hydrophobic interaction chromatography (HIC) is a separation method that takes advantage of the hydrophobic properties of the proteins. The adsorption is promoted by the hydrophobic interactions between non-polar regions on the protein and immobilized hydrophobic ligands on a solid support. Adsorption is achieved at high salt concentrations in the aqueous mobile phase and elution is facilitated by decreasing the salt concentration. The hydrophobic interaction chromatography material is a matrix substituted with hydrophobic ligands such as ethyl-, butyl-, phenyl- or hexyl-groups. Preferred material is a matrix substituted with a butyl or a phenyl ligand.

Hydrophobic Interaction Chromatography (HIC) resins are known in the art and include resins such as BUTYL SEPHAROSE (GE Healthcare), PHENYL SEPHAROSE (low and high substitution), OCTYL SEPHAROSE and ALKYL SEPHAROSE (all of GE Healthcare; other sources of HIC resins include Biosepra, France; E. Merck, Germany; BioRad USA).

In a preferred embodiment, the hydrophobic interaction chromatography is carried out with a resin such as BUTYL SEPHAROSE HP (obtainable from GE Healthcare). It is understood that step (c) may be performed using alternate resins, having similar characteristics. Alternative resins that may be used are as follows: TOYOPEARL BUTYL 650M (obtainable from Tosoh Biosep Inc.), PHENYL SEPHAROSE 6 FAST FLOW (low sub); PHENYL SEPHAROSE 6 FAST FLOW (high sub); BUTYL SEPHAROSE 4 FAST FLOW; OCTYL SEPHAROSE 4 FAST FLOW; PHENYL SEPHAROSE HIGH PERFORMANCE; SOURCE 15ETH; SOURCE 15ISO; SOURCE 15PHE all from GE Biosciences (800) 526-3593. Still further resins are: HYDROCELL C3 or C4; HYDROCELL PHENYL from BioChrom Labs Inc. (812) 234-2558; (see www.biochrom.com).

In a preferred embodiment the equilibration, loading, wash and elution buffer is selected from the group consisting of sodium phosphate, MES, Bis-Tris, ADA, PIPES, ACES, BES, MOPS, TES, HEPES, preferably sodium phosphate. Binding on the HIC resin is in general achieved by using an equilibration and loading buffer with a high conductivity, obtained e.g. through the addition of salt such as NaCl, $(NH_4)_2SO_4$ or $Na_2SO_4$, preferably ammonium sulfate. Preferred salt concentrations are 1 to 2M, preferably about 1.5M $(NH_4)_2SO_4$. The wash generally uses the loading buffer. Elution in the step of hydrophobic interaction chromatography is preferably carried out by reducing the conductivity of the mobile phase (reducing salt concentration). The reduction can be achieved in a linear way or step-wise.

It is preferred using an equilibration, loading, wash and elution buffer having a pH at or about 6 to at or about 9, more preferably at or about 7.0 to at or about 8.5 most preferably at or about 7.5. A particularly preferred equilibration, loading and wash buffer system contains sodium phosphate and ammonium sulfate preferably at a pH of at or about 7.5. A preferred elution buffer contains sodium phosphate at a pH at or about 7.5.

In a particularly preferred embodiment, the product-contacting buffers for the step (c) of HIC (equilibration, load, wash, elution) contain an antioxidant, such as L-methionine. Alternative antioxidants include t-butyl-4-methoxyphenol, 2,6-bis(1,1-dimethylethyl)-4-methyl phenol; potassium or sodium bimetabisulfite, sodium bisulfite.

Additional Steps

Further to the three main chromatography steps (a), (b) and (c) the process of the present invention may optionally include additional steps known to the person skilled in the art, e.g. chromatography steps, filtration steps or virus inactivation steps. Preferred additional steps are ion exchange chromatography such as anion exchange chromatography or cation exchange chromatography, affinity chromatography such as dye affinity chromatography, immune affinity chromatography, lectin affinity chromatography or perborate affinity chromatography, filtration such as diafiltration, ultrafiltration or nanofiltration, or virus inactivation.

Anion Exchange Chromatography Step (d)

In a preferred embodiment the process of the present invention in addition comprises an anion exchange chromatography (d). The anion exchange chromatography is usually performed by equilibrating and loading the column, followed by a wash and subsequent elution.

The anion exchange chromatography is carried out, preferably with a quaternary ammonium resin, such as CAPTOQ (obtainable from GE Healthcare), or a resin having similar characteristics such as TOYOPEARL QEA (obtainable from Tosoh), Q SEPHAROSE FF (obtainable from GE Healthcare) or FRACTOGEL EMD, FRACTOGEL TMAE or FRACTOGEL HICAP (obtainable from Merck KGaA, Darmstadt Germany).

The anion exchange chromatography resin is preferably equilibrated, loaded and washed by using a buffer having a mildly alkaline pH, e.g. at or about 7.2 to at or about 9.0, or at or about 8.0 to at or about 9.0, most preferably at or about 8.5. Suitable buffers include, for example borate buffer, triethanolamine/iminodiacetic acid, Tris (2-Amino-2-hydroxymethyl-propane-1,3-diol), sodium phosphate, ammonium acetate, tricine (N-(Tri(hydroxymethyl)methyl)glycine), bicine (2-(bis(2-hydroxyethyl)amino)ethanoic acid), TES, HEPES, TAPS(N-Tris(hydroxymethyl)methyl-3-aminopropanesulfonic acid). Most preferred is ammonium acetate, at a pH of at or about 8.5.

Elution from the ion-exchange resin is achieved by increasing the conductivity of the mobile phase through the addition of salt, preferably NaCl. Suitable buffers include, for example borate buffer, triethanolamine/iminodiacetic acid Tris, ammonium acetate, tricine, bicine, TES, HEPES, TAPS. Preferred is ammonium acetate.

The anion exchange chromatography can be utilized to selectively elute different charge isoforms mainly originating from different sialylation and/or sulfation levels of the glycan-moieties of the glycoprotein.

Glycoproteins are build up from a peptide backbone and oligosaccharides either attached to the OH-group of serine and/or threonine residues in an O-linked fashion and/or attached to the amide group of asparagine in an N-linked fashion. The oligosaccharide structures often terminate with the negatively charged saccharide neuraminic acid (also named sialic acid).

The in vivo activity of glycoprotein products seems to be influenced by the degree of sialylation of terminal galactose. For instance De Leeuw et al. (1996, Mol Hum Reprod. 1996 May; 2(5):361-9) showed that FSH isoforms with high sialic acid content exerted higher specific activity than those with lower sialic acid content due to a prolonged circulating half life. However, FSH isoforms having a lower sialic acid content show a higher receptor binding activity. Therefore, for specific applications of FSH, different isoforms with different sialylation degrees may be required.

The term "isoform", as used herein, refers to a glycoprotein preparation/fraction that contains glycoproteins which have identical or very similar amino acid sequence and a common isoelectric point but which may differ in respect to the extent, to the complexity, to the nature, to the antennarity and to the order of attached galactosyl- and sialyl-groups. An isoform according to the invention may also comprise multiple glycoprotein forms of the same or very similar amino acid sequence and isoelectric point which differ additionally in other charge carrying modifications such as acetylation and sulfation. The term "very similar amino acid sequence" indicates that the amino acid sequence of a protein also comprises those sequences that are functionally equivalent to the wild type amino acid sequence and thus, exert the same function. In particular, "very similar amino acid sequence" shares a sequence homology, preferably a sequence identity, with a reference amino acid sequence of at least 70%, preferably at least 80%, at least 90%, at least 95%, most preferably at least 98%, over a stretch of consecutive amino acids representing at least 50%, preferably at least 70%, at least 80%, at least 90%, at least 95%, more preferably 100% of the entire reference amino acid sequence.

Thus, glycoprotein isoforms preferably can be defined by their isoelectric point and amino acid sequence and each such defined isoform may actually comprise multiple isoforms in the strict chemical sense (molecules having the same atomic composition but differing in their spatial structure). In particular, the isoelectric point of different glycoproteins of the same isoform preferably does not differ by more than 2 units, more preferable not more than 1 unit, not more than 0.5 units or not more than 0.2 units, and most preferably the isoelectric point does not differ by more than 0.1 units.

For the selective elution of differently charged isoforms such as differently sialylated isoforms it is preferred to use two or more, preferably two elution buffers A and B which differ in pH and/or salt content, each of them being based on e.g. ammonium acetate, borate buffer, triethanolamine/iminodiacetic acid, Tris, sodium phosphate, ammonium acetate, tricine, bicine, TES, HEPES or TAPS, preferred is ammonium acetate. Using different elution buffers, elution can be performed in a stepwise fashion, first using one elution buffer and then using the other elution buffer, optionally also using one or more intermediate elution steps with different mixtures of the elution buffers. Alternatively or additionally, elution can be performed using a gradient, starting with a first mixing ratio of the elution buffers (e.g. 100% of the first elution buffer) and gradually changing to a second mixing ratio of the elution buffers (e.g. 100% of the second elution buffer).

The elution buffer used first (buffer A) in general can be a) a mildly acidic buffer which is salt-free, or b) a neutral or mildly basic buffer with low salt content such as NaCl (preferably between 20 and 200 mM). Buffer A can be used to elute glycoprotein of low charge, e.g. low degree of sialylation. In variant a) buffer A has a pH e.g. at or about 3.0 to at or about 6.5, or at or about 4.0 to at or about 6.0, most preferably at or about 5. In variant b) buffer A has a pH e.g. at or about 7.0 to 9.0, preferably 8.5.

The elution buffer used second (buffer B) in general is a salt-containing mildly alkaline buffer of a higher salt content than buffer A which can be used to elute glycoprotein of high charge, e.g. high degree of sialylation. Buffer B has a pH e.g. at or about 7.0 to at or about 9.0, or at or about 8.0 to at or about 9.0, most preferably at or about 8.5. The salt is preferably NaCl. The salt content in buffer B is preferably from 200 mM to 1M.

Using different elution buffers and a gradient or stepwise elution, the different glycoprotein isoforms loaded onto the anion exchange chromatography column will elute in different fractions depending on their charge. For example, the glycoprotein to be purified may be present in the fractions of the flow-through, i.e. it binds to the anion exchange chromatography column only weakly or not at all, it may be eluted with the first elution buffer, at a specific mixing ratio of the first and second elution buffer, or with the second elution buffer. The glycoprotein fractions which are used for the further purification steps and thus, the glycoprotein isoforms which are to be purified, mainly depend on the desired applications of the glycoprotein. The other glycoprotein isoforms which are not of interest can be removed using the anion exchange chromatography step. With respect to FSH, for example only FSH having a high degree of sialylation and thus, having a high circulation half-life, or only FSH having a low degree of sialylation and thus, having a high receptor binding activity, may be purified.

In a particularly preferred embodiment the product-contacting buffers for the ion-exchange chromatography (equilibration, wash, elution) contain an antioxidant, preferably L-methionine. Alternative antioxidants are mentioned above.

As an alternative or additionally to standard anion exchange chromatography, chromatofocusing can be performed. Chromatofocusing is a chromatography technique that separates proteins according to differences in their isoelectric point (pI). In particular, a charged stationary phase can be used and the proteins loaded onto the chromatofocusing column can be eluted using a pH gradient. For example, the stationary phase may be positively charged and the pH gradient may develop from a first pH to a second, lower pH, for example from about pH 9 to about pH 6 or from about pH 7 to about pH 4. Due to the specific conditions of the chromatofocusing, proteins elute in order of their isoelectric points and preferably proteins of a specific pI are focused into narrow bands. This, as proteins at a pH higher than their pI are negatively charged and attach to the positively charged stationary phase, thereby being slowed down. When the pH in the elution gradient reaches the pI of the protein, it is overall neutral in charge and thus migrates with the flow of the mobile phase. At a pH lower than the pI of the protein, the protein is repulsed by the stationary phase due to its positive charge, thus accelerating it. Thereby proteins at the rear of a zone will migrate more rapidly than those at the front, gradually forming narrower bands of proteins. In this setting, the protein with the highest pI elutes first and the protein with the lowest pI will elute last.

Suitable stationary phases are, for example, media substituted with charged, buffering amines such as MONO P (obtainable from GE Healthcare) or other anion exchange chromatography material. For forming the pH gradient for elution, suitable buffing systems such as POLYBUFFER 74 or POLYBUFFER 76 (obtainable from GE Healthcare) can be used. Equilibration, loading and washing of the column can be done using any condition where the glycoprotein of interest and/or any impurities bind to the column material. For example, conditions as described above for the anion exchange chromatography can be used. When using a decreasing pH gradient, preferably a buffer having a pH equal to or higher than the starting pH of the elution gradient is used for equilibration, loading and/or washing. When using an increasing pH gradient, preferably a buffer having a pH equal to or lower than the starting pH of the elution gradient is used for equilibration, loading and/or washing.

Preferably, for equilibration, loading and washing, a buffer similar to that used at the beginning of the elution pH gradient is used.

Overall Process

The steps of reverse phase chromatography, size exclusion chromatography, hydrophobic interaction chromatography and anion-exchange chromatography may be carried out in any order, although it is preferred to carry out a step of reverse phase chromatography first. The remaining steps may be carried out in any order, although it is preferred to follow the order of (1) reverse phase chromatography, (2) size exclusion chromatography, (3) anion exchange chromatography, (4) hydrophobic interaction chromatography. Optional is a subsequent concentration and/or buffer exchange step (5) of ultrafiltration and/or diafiltration, and a step (6) of nanofiltration.

In preferred embodiments, the process for the purification of a glycoprotein according to the invention does not comprise an immunoaffinity chromatography and/or a cation exchange chromatography. More preferably, the process according to the invention does not comprise any further chromatographic steps except of those described herein. The process according to the invention preferably comprises only three chromatographic steps, i.e. a reverse phase chromatography, a size exclusion chromatography and a hydrophobic interaction chromatography, or only four steps, i.e. a reverse phase chromatography, a size exclusion chromatography, an anion exchange chromatography and a hydrophobic interaction chromatography. The anion exchange chromatography may also be replaced by a chromatofocusing step as described above.

However, further non-chromatographic steps, preferably those described herein, may be performed in addition to and also between the steps defined. Preferably, these further steps include steps for diminishing or inactivation undesired or hazardous substances such as bacteria, viruses, nucleic acids or prion proteins, for example sterile filtration, nanofiltration, adsorption and/or pH inactivation steps. In alternative embodiments, besides the steps described above, the process according to the invention may comprise chromatographic steps for diminishing or inactivation undesired or hazardous substances, including for example adsorption chromatography. Preferably, the purification process of the invention comprises at least one, more preferably at least two, most preferably at least three virus diminishing or inactivation steps. In this respect, also the chromatography steps of the purification process according to the invention, in particular the size exclusion chromatography step (b), may be used as virus diminishing step since they normally separate viruses from the glycoprotein. For example, viruses and virus-like particles have a much bigger size compared to glycoproteins and thus, are effectively separated therefrom during size exclusion chromatography.

Furthermore, the process according to the invention preferably does not comprise a buffer exchange step directly prior to and/or directly subsequent to the size exclusion chromatography. In particular, if the process is performed in the order of (1) reverse phase chromatography, (2) size exclusion chromatography, optional (3) anion exchange chromatography, and (4) hydrophobic interaction chromatography, preferably there is no buffer exchange between the reverse phase chromatography and the size exclusion chromatography and/or between the size exclusion chromatography and the anion exchange chromatography or the hydrophobic interaction chromatography.

Other Steps

Prior to the first chromatography step (particularly prior to a step of reverse phase chromatography), it may be desirable to carry out a step of ultrafiltration, in order to concentrate the crude glycoprotein. Furthermore, additionally a step of diafiltration may be performed prior to the first chromatography step in order to perform a buffer exchange. The ultrafiltration step and the diafiltration step may be performed simultaneously or sequentially. The ultrafiltration and/or diafiltration is preferably carried out using a membrane having a cut-off of at or about 3-30 kD, most preferably at or about 10 kD. However, the present invention also encompasses purification processes wherein no ultrafiltration step and/or no diafiltration step is performed prior to the first chromatography step.

In a preferred embodiment, after one or more of the steps of chromatography (particularly after the last step of chromatography), the glycoprotein sample is subjected to an ultrafiltration and/or diafiltration step. Preferably the ultrafiltration and/or diafiltration is performed in order to obtain a bulk having the desired composition. The ultrafiltration (and/or diafiltration) is preferably carried out using a membrane having a cut-off of at or about 3-30 kD, most preferably at or about 10 kD. It is preferred to perform during ultrafiltration and/or diafiltration a buffer exchange to a pre-formulation buffer, e.g. selected from the group consisting of sodium phosphate, sodium citrate, MES, Bis-Tris, ADA, PIPES, ACES, BES, MOPS, TES, HEPES, preferably sodium phosphate, preferably sodium-phosphate containing stabilizers e.g. sucrose and antioxidants like L-methionine. The pH preferably is in the range of 6.5 to 7.5, more preferably about 7.0 to 7.1.

Further optional steps which can be performed in the purification process according to the invention include one or more sterile filtration steps. These steps can be used to remove biological contaminations such as eukaryotic and/or prokaryotic cells, in particular bacteria, and/or viruses. Preferably, these steps are preformed at or near the end of the purification process to prevent a further contamination after the sterile filtration step. For removal of bacteria or other cells, the filter used for sterile filtration preferably has a pore size of 0.22 µm or less, preferably 0.1 µm or less. For removal of viruses or virus-like particles, a nanofiltration step as described below may be performed.

Another additional step which can be performed in the purification process according to the invention is a virus inactivation step via incubation of the glycoprotein at a specific pH. For example, the glycoprotein is incubated at a pH of 4.0 or less, preferably at about pH 3.6. The incubation time preferably is at least 15 min, at least 30 min, at least 60 min, at least 90 min, at least 2 h, at least 3 h or at least 6 h. Incubation may be performed at low temperature such as 10° C. or less or 4° C. or less, or at about room temperature. For example, the glycoprotein material may be incubated at a pH of about 3.6 for about 90 min at about room temperature. This virus inactivation step can be performed at any time during the purification process and preferably is performed after the last chromatography step.

In one preferred embodiment, the process of the present invention comprises the following steps in the order shown below:
(0) Ultrafiltration (optionally an additional diafiltration step; preferably with a membrane having a cut-off of at or about 10 kD);
(1) Reverse phase chromatography (RPC) (preferably using a Source 30 RPC column);
(1a) Ultrafiltration (preferably with a membrane having a cut-off of at or about 10 kD);
(2) Size exclusion chromatography (preferably using a Superdex 200 column);
(3) Anion-exchange chromatography (preferably using a CaptoQ column);
(4) Hydrophobic interaction chromatography (HIC) (preferably using a Butyl HP column);
(5) Ultrafiltration and/or diafiltration (preferably with a membrane having a cut-off of 10 kD).

It may be desirable to subject the glycoprotein sample to a step of nanofiltration, in particular as a virus clearance step; i.e. to reduce the risk of contamination of the glycoprotein preparation with viruses or virus-like particles originating from the cell culture. Nanofiltration may be performed at any stage of the purification process, however, it is particularly preferred to carry out nanofiltration after the end of the chromatographic procedure. Nanofiltration may be performed more than one time, for example it may be performed twice. Preferred nanofiltration devices have a pore size of about 15 to 20 nm.

In another preferred embodiment, the method of the invention thus comprises the following steps in the order shown below:

(0) Ultrafiltration (preferably with a membrane having a cut-off of at or about 10 kD),
(1) Reverse phase chromatography (RPC) (preferably using a Source 30 RPC column)
(1a) Ultrafiltration (preferably with a membrane having a cut-off of at or about 10 kD),
(2) Size exclusion chromatography (preferably using a Superdex 200 column);
(3) Anion-exchange chromatography (preferably using a CaptoQ column);
(4) Hydrophobic interaction chromatography (HIC) (preferably using a Butyl HP column);
(5) Ultrafiltration and/or diafiltration (preferably with a membrane having a cut-off of 10 kD);
(6) Nanofiltration (preferably including virus clarification).

The specific purification processes described above are preferably performed without including any further chromatography steps and/or ultrafiltration steps and/or diafiltration steps. However, in particular embodiments, the purification processes described above may further comprise additional steps, in particular one or more of the additional steps described herein, for example those used for removing or inactivating undesired or and/or hazardous substances.

It is preferred that an antioxidant or a free amino acid or dipeptide with antioxidant and scavenging effect is included in some or all of the steps of the purification method according to the present invention. More specifically the antioxidant is present in any of the buffers used to purify and/or concentrate and/or filter the glycoprotein such as FSH. The antioxidant prevents oxidation of the glycoprotein such as FSH during processing. A preferred antioxidant is L-methionine. Preferably, L-methionine is used at a concentration of at or about 0.1 to 10 mM. Further examples of an antioxidant include t-butyl-4-methoxy-phenol, 2,6-bis(1,1-dimethylethyl)-4-methyl phenol; potassium or sodium bimetabisulfite, sodium bisulfite. Examples of free amino acid and dipeptide with antioxidant and scavenging effect are histidine, taurine, glycine, alanine, carnosine, anserine, 1-methylhistidine or combinations thereof.

An advantage of the present invention is that the purification process is highly effective, reduces the number chromatographic steps to a minimum of 3 chromatographic steps or—including an enrichment of highly sialylated glycoprotein molecules—to a minimum of 4 chromatographic steps. In particular, using the purification process according to the invention, cost intensive and problematic purification steps such as in particular affinity purification steps, especially immunoaffinity purification steps, become unnecessary and can be avoided. The process provides a high degree of glycoprotein purity and specific bioactivity >90%, preferably >98%, more preferably >99% w/w, each based on total protein as measured, for example, by HCP-ELISA. Furthermore, the purification process according to the invention provides a surprisingly high recovery of the glycoprotein of interest present in the starting material.

The Glycoproteins

Glycoproteins are proteins that contain oligosaccharide chains (glycans) covalently attached to polypeptide sidechains. Glycoproteins may comprise one or more glycans which preferably are coupled to a nitrogen atom (N-glycosylation) or an oxygen atom (O-glycosylation) of the polypeptide. Thus, the glycoprotein may be N-glycosylated and/or O-glycosylated. Preferably, the glycoproteins comprise natural glycans. However, the term "glycoprotein" comprises proteins or polypeptides having natural glycans and/or non-natural glycans, in particular synthetically produced glycans and/or glycans comprising non-natural or modified monosaccharide unit(s).

The glycoprotein to be purified is preferably selected from the group of gonadotropins such as FSH (follicle-stimulating hormone), CG (chorionic gonadotropin), LH (luteinizing hormone) and TSH (thyroid-stimulating hormone) including all isoforms and variants thereof. The terms "glycoprotein", "FSH", "CG", "LH" and "TSH" as used in this application always include all isoforms and variants of the glycoprotein, especially those described below and under step (d) (AEX) above. The term "gonadotropin" according to the invention preferably refers to the natural gonadotropins such as FSH, CG, LH and TSH but also to recombinant versions thereof as well as to any isoforms, variants and analogues thereof. Preferably, the isoforms, variants and analogues of gonadotropins exhibit one or more biological activities of the natural gonadotropins. However, the process for purification of a glycoprotein according to the invention is also suitable for purifying other glycoproteins such as, for example, erythropoietin, various antibodies, in particular monoclonal antibodies, granulocyte macrophage-colony-stimulating factor, and tissue plasminogen activator.

Storage/Lyophilisation

The liquid composition resulting from the purification process as described above and containing purified glycoprotein may be frozen for storage as is, or after purification, the eluate may be subjected to lyophilisation ("freeze-drying") to remove solvent. The resulting liquid or lyophilised product is termed "Glycoprotein Bulk".

Formulations

The glycoprotein of the invention or purified according to the method of the invention may be formulated for any kind of administration, preferably for injection, either intramuscular or subcutaneous, preferably subcutaneous. The glycoprotein formulation may be freeze-dried, in which case it is dissolved in water for injection just prior to injection. The glycoprotein formulation may also be a liquid formulation, in which case it can be injected directly, without prior dissolution. The formulation may contain known excipients and stabilizers and may additionally comprise antioxidants and/or surfactants. The glycoprotein formulation may be single dose or multiple dose. If it is multiple dose, it should preferably contain a bacteriostatic agent, such as, for example, alkylparabene, benzyl alcohol, meta-cresol, thymol or phenol, preferably methylparabene or meta-cresol. Single dose formulations may also comprise a bacteriostatic agent. Suitable formulations are described e.g. in WO 2004/087213, WO 00/04913, WO 2007/092829 and EP 0 853 945, herein incorporated by reference.

The glycoprotein of the invention may be formulated with known excipients and stabilizers, for example, sucrose and mannitol. It may also comprise an antioxidant, such as methionine. It may further comprise a surfactant, such as TWEEN (preferably TWEEN 80), or PLURONIC (preferably PLURONIC F68).

In a particularly preferred multidose formulation, the glycoprotein produced by the method of the invention is formulated by dissolving it in water for injection with sucrose, phosphate buffer (pH 6.5 to 7.5), Pluronic F68, methionine and a bacteriostatic agent.

Indications

The glycoprotein of the invention is suitable for use in all treatments where the glycoprotein is indicated. For instance FSH is particularly suited for subcutaneous administration in ovulation induction, controlled ovarian hyperstimulation for assisted reproductive technologies, and in the treatment of oligospermia. It may be used in conjunction with other gonadotropins, such as LH and CG. It may also be used with further compounds which augment the response to FSH, such as clomiphene citrate, aromatase inhibitors, such as Anastrozole, Letrozole, Fadrozole and YM-511. Furthermore, LH and CG may also be used alone in fertility treatment.

Recombinant Glycoproteins

The use of the term "recombinant" refers to preparations of glycoprotein such as FSH that are produced through the use of recombinant DNA technology. One example of a method of expressing a glycoprotein using recombinant technology is the transfection of a suitable host cell, preferably a eukaryotic host cell, with an expression vector comprising a DNA sequence encoding the glycoprotein of interest. Usually, the expression vector carries a strong promoter driving the expression of the glycoprotein, e.g. CMV or SV40 and a suitable selection marker for selecting host cells that have incorporated the vector. Transfection can be stable or transient. Suitable recombinant expression systems are well-known in the prior art and thus need no detailed description. Preferably, the eukaryotic host cell is selected from primate cells, preferably human cells and rodent cells, preferably CHO cells. For recombinant expression of FSH, the eukaryotic host cells are transfected with DNA sequences encoding an alpha and beta subunit of FSH, whether provided on one vector or on two vectors with each subunit having a separate promoter, as described in European patent nos. EP 0 211 894 and EP 0 487 512. The DNA encoding FSH may be a cDNA or it may contain introns.

Another example of the use of recombinant technology to produce FSH is by the use of homologous recombination to insert a heterologous regulatory segment in operative connection to endogenous sequences encoding one or both of the subunits of FSH, as described in European patent no. EP 0 505 500 (Applied Research Systems ARS Holding NV). Also contemplated are methods such as those disclosed in WO 99/57263 (Transkaryotic Therapies), wherein one of the subunits is inserted heterologously into a cell, and the other subunit is expressed by activation of genomic sequences by insertion of a heterologous regulatory segment by homologous recombination. The method of the invention may be used to purify FSH expressed using any of these methods and other methods.

The purification process according to the invention is useful for purifying natural as well as recombinant glycoproteins, including isoforms and variants thereof. Glycoprotein isoforms preferably refer to isoforms as defined above. The term "variant" preferably encompasses glycoproteins derived from a natural glycoprotein, such as mutant forms thereof, fusion proteins thereof, fragments thereof and/or glycoproteins having a different glycosylation pattern. Also mimetic compounds of the glycoproteins are comprised, including proteins comprising glycomimetic structures and/or peptidomimetic structures. Preferably, the glycoprotein variants and/or isoforms exhibit one or more activities which are qualitatively and/or quantitatively similar or identical to those of the natural glycoprotein.

The expression "glycoprotein variant" such as "FSH variant" is meant to encompass those molecules differing in amino acid sequence, number of glycosylation sites (including additional or deleted glycosylation sites) or in inter-subunit linkage from human glycoprotein but exhibiting one or more of its activities. Examples of FSH variants include CTP-FSH, a long-acting modified recombinant FSH, consisting of the wild type [alpha]-subunit and a hybrid [beta]-subunit in which the carboxy terminal peptide of hCG has been fused to the C-terminal of the [beta]-subunit of FSH, as described in LaPolt et al.; Endocrinology; 1992, 131, 2514-2520; or Klein et al.; Development and characterization of a long-acting recombinant hFSH agonist; Human Reprod. 2003, 18, 50-56]. Also included is single chain CTP-FSH, a single chain molecule, consisting of the following sequences (from N-terminal to C-terminal):

[beta]FSH, [beta]hCG CTP (113-145), [alpha]FSH wherein [beta]FSH signifies the [beta]-subunit of FSH, [beta] hCG CTP (113-145) signifies the carboxy terminal peptide of hCG and [alpha]FSH signifies the [alpha]-subunit of FSH, as described by Klein et al. [Pharmacokinetics and pharmacodynamics of single-chain recombinant human follicle-stimulating hormone containing the human chorionic gonadotrophin carboxyterminal peptide in the rhesus monkey, Fertility & Sterility; 2002, 77, 1248-1255]. Other examples of FSH variants include FSH molecules having additional glycosylation sites incorporated in the [alpha]- and/or [beta]-subunit, as disclosed in WO 01/58493 (Maxygen), and FSH molecules with intersubunit S—S bonds, as disclosed in WO 98/58957. Further examples of FSH variants include chimeric molecules comprising sequences from FSH and sequences from hCG or LH, such as those described in WO 91/16922 and WO 92/22568.

The FSH variants referred to herein also include the carboxy terminal deletions of the beta subunit that are shorter than the full length mature protein. It is understood that the carboxy terminal variants of the beta chain form complex with a known alpha subunit to form an FSH variant heterodimer. Furthermore, FSH variants also include fusion proteins wherein the α-chain and the β-chain or parts thereof are combined in one polypeptide chain, preferably comprising a linker between both chains. In other examples of FSH fusion proteins one or both of the FSH chains is/are fused to an antibody or a part thereof such as an Fc fragment of an antibody.

The FSH variants referred to herein also include FSH from different species like e.g. horse (*Equus caballus*), pig (*Sus scrofa*), cow (*Bos taurus*), cat (*Felis catus*), dog (*Canis familiaris*).

In a preferred embodiment, the FSH is produced recombinantly, either in a serum or in a serum-free medium. In another preferred embodiment, the purified FSH produced according to the method of the invention is suitable for subcutaneous administration, permitting self-administration by the patient.

The variants of the glycoprotein described above with respect to FSH as exemplary glycoprotein in a similar manner also apply to other glycoproteins, where appropriate, in particular to other gonadotropins such as LH, TSH and CG.

The expression "crude recombinant glycoprotein" refers to the cell culture supernatant from recombinant cells expressing glycoprotein, before it has undergone any chromatographic step. The expression encompasses the raw form of the supernatant (as isolated from cells) as well as concentrated and/or filtered and/or ultrafiltered supernatant.

Process for Manufacturing Glycoproteins

Also provided is a process for manufacturing a glycoprotein of interest by performing the process for the purification of a glycoprotein described herein. The glycoprotein can be obtained from natural sources or recombinantly.

In a preferred embodiment, a process for manufacturing a glycoprotein of interest is provided, comprising the following steps:
  i) recombinantly expressing the glycoprotein of interest;
  ii) purifying said recombinantly expressed glycoprotein of interest by subjecting a liquid containing said glycoprotein at least to the steps of:
    a) reverse phase chromatography,
    b) size exclusion chromatography, and
    c) hydrophobic interaction chromatography.

The respective manufacturing process leads to the production of very pure glycoproteins which are in particular suitable for use in pharmaceutical formulations.

Said manufacturing process preferably comprises at least one or more steps as described above in conjunction with the purification process. The respective disclosure also applies to the manufacturing process according to the present invention and it is referred to the above disclosure to avoid repetitions.

Furthermore, the manufacturing process according to the present invention may comprise a step of formulating the glycoprotein of interest in form of a pharmaceutical formulation. Suitable liquid or lyophilised formulations are known in the prior art and are described above, we refer to the respective disclosure.

Preferably, the glycoprotein of interest that is produced by the manufacturing method according to the present invention is selected from the gonadotropins, preferably selected from FSH, CG, LH and TSH.

Experimental Section

The following experiment illustrates the process of the present invention and in no way is intended to limit the disclosure.

Step 0: Ultrafiltration

The crude FSH forming the starting material was derived from cell culture supernatants containing recombinant FSH.

Prior to the Ultrafiltration step the supernatant was clarified by room temperature filtration through a 2 μm depth filter. Then ultrafiltration was then performed with a membrane having a cut-off of at or about 10 kD, with a transmembrane pressure not exceeding 1.2 bar.

Step 1: Reverse Phase Chromatography (SOURCE30 RPC Column)

Loading buffer: 20 mM Na-phosphate pH 7.5/10% v/v isopropanol (containing methionine)

Elution buffer: 20 mM Na-phosphate pH 7.5/18% v/v isopropanol (containing methionine)

The material obtained from the concentration and ultrafiltration (step 0) was supplemented with isopropanol at a concentration equivalent to the loading buffer. The SOURCE30 column is equilibrated with loading buffer. After loading the material onto the column unbound material is washed out for about 15CV by loading buffer. The FSH is eluted by increasing the isopropanol concentration up to 18% v/v in the Elution Buffer (about 8CV). The elution pool is concentrated by ultrafiltration to proceed to the next step. The step is performed at room temperature.

| RPC | |
|---|---|
| Column | SOURCE 30 RPC |
| | Polystyrene/divinyl benzene |
| Bonded phase | None |
| Bead form | Rigid, spherical, porous, monodisperse |
| Particle size | 30 μm |
| Residence [min] | 1.3 |
| max in Flow [cm/h] | 500 |

Step 1a: Ultrafiltration

The eluate from step 1 (RPC) was subjected at room temperature to ultrafiltration with a membrane having a cut-off of at or about 10 kD at a transmembrane pressure not exceeding 1.2 bar and concentrating the eluate to about 10% of the SEC column volume.

Step 2: Size Exclusion Chromatography (SUPERDEX 200 Column)

Running buffer: 15 mM ammonium-acetate pH 8.5 (containing methionine)

The pooled material from step 1a was subjected to the SEC column, equilibrated with running buffer. FSH is eluted under isocratic conditions at a distinct retention time (about 0.6-0.7 CV). This chromatography step provides purification and a buffer exchange prior to the next step. The SEC step is performed at room temperature.

| SEC | |
|---|---|
| Column | SUPERDEX 200 |
| | Spherical composite of cross-linked agarose and dextran |
| Bed height | 60 cm |
| Exclusion limit ($M_r$) | $1.3 \times 10^6$ globular protein |
| Separation range ($M_r$) | 10 000-600 000 globular protein |
| max lin. Flow [cm/h] | 120 |

Step 3: Anion-Exchange Chromatography (CAPTOQ Column)

Loading buffer: 15 mM ammonium-acetate pH 8.5 (containing methionine)

Elution buffer A: 15 mM ammonium-acetate pH 5 (containing methionine)

Elution buffer B: 15 mM ammonium-acetate pH 8.5 (containing methionine)-0.25 M NaCl The material obtained from step 2 (SEC) was then applied to an anion exchange resin equilibrated with loading buffer. The unbound material was washed out with loading buffer (about 10 CV). FSH was partly eluted by elution buffer A (containing the less charged FSH molecules) prior to the second elution step with elution buffer B (containing the higher charged FSH molecules). Both elution steps are performed in a stepwise fashion. The AEX is performed at room temperature.

| AEX | |
|---|---|
| Matrix | CAPTOQ |
| Ion exchange type | strong anion, Q |
| Charged group | $-N^+ (CH_3)_3$ |
| Total ionic capacity | 0.16-0.22 mmol $Cl^-$/ml medium |
| Particle size* | 90 μm (d50v) |
| Max. Lin Flow | 700 cm/h |
| Dynamic binding capacity | >100 mg BSA/ml medium |

Step 4: Hydrophobic Interaction Chromatography (HIC) (Butyl HP column)

Loading buffer: 20 mM Na-phosphate pH 7.5-1.5 M ammonium-sulfate (containing methionine)

Elution buffer: 20 mM Na-phosphate pH 7.5 (containing methionine)

The material from elution with buffer B obtained from the anion-exchange chromatography column (higher acidic FSH molecules) was adjusted with loading buffer to 1.5 M ammonium-sulfate and loaded onto a Butyl-HP SEPHAROSE column equilibrated with loading buffer. After washing out the unbound material, FSH was eluted from the column by decreasing the ammonium-sulfate concentration in a linear fashion down to zero. The HIC step is performed at room temperature.

| HIC | |
|---|---|
| Matrix | Butyl Sepharose HP |
| Ligand | Butyl |
| Ligand density | 50 μmol/ml |
| Average particle size | 34 μm |
| max lin Flow | 600 cm/h |

Step 5: Diafiltration (Membrane Having a Cut-Off of 10 kD)
Preformulation buffer:
9-10 mM sodium-phosphate pH 7.0-7.1
0.1 g/l methionine
50 mg/ml Sucrose The eluate from step 4 (HIC) was then applied at room temperature to diafiltration. By this step buffer is exchanged to preformulation buffer and adjusted to the desired concentration.

Step 6: Nanofiltration

The product from the diafiltration step was directly applied to a 20 nm nanofiltration device at a pressure of about 2 bar. The step was performed at room temperature.

The process of steps (−1) to (6) rendered FSH at a purity of >99.99% w/w based on total protein as determined by HCP-Assay (host cell protein level <0.01% w/w).

The invention claimed is:

1. A process for the purification of a gonadotropin comprising subjecting a biological sample containing the gonadotropin to the steps of:
   a) reverse phase chromatography as a first chromatographic step,
   b) size exclusion chromatography, and
   c) hydrophobic interaction chromatography;
   wherein the steps are performed in the sequence of reverse phase chromatography, size exclusion chromatography, and hydrophobic interaction chromatography.

2. The process according to claim 1, wherein in reverse phase chromatography step (a), the elution buffer contains an organic solvent.

3. The process according to claim 1, wherein in size exclusion chromatography step (b), a buffer exchange is performed.

4. The process according to claim 1, further comprising one or more steps selected from the group consisting of chromatography steps, filtration steps and virus inactivation steps.

5. The process according to claim 1, further comprising one or more steps elected from the group consisting of ion exchange chromatography, affinity chromatography, diafiltration, ultrafiltration, nanofiltration and virus inactivation.

6. The process according to claim 1, further comprising an anion exchange chromatography step.

7. The process according to claim 6, wherein the anion exchange chromatography step is carried out subsequent to size exclusion chromatography step b).

8. The process according to claim 6, wherein at least one salt-containing elution buffer is used in the anion exchange chromatography step.

9. The process according to claim 6, wherein different charged isoforms of the glycoprotein are separated.

10. The process according to claim 1, wherein the gonadotropin is selected from the group consisting of follicle-stimulating hormone (FSH), chorionic gonadotropin (CG), luteinizing hormone (LH) and thyroid-stimulating hormone (TSH).

11. The process according to claim 1, wherein the gonadotropin is produced recombinantly.

12. A process for the purification of a gonadotropin comprising subjecting a biological sample containing the gonadotropin to the sequential steps of:
   (0) Ultrafiltration;
   (1) Reverse phase chromatography as a first chromatographic step;
   (1a) optionally Ultrafiltration;
   (2) Size exclusion chromatography;
   (3) Anion-exchange chromatography;
   (4) Hydrophobic interaction chromatography;
   (5) Ultrafiltration and/or diafiltration;
   (6) Nanofiltration.

13. A process for manufacturing a gonadotropin of interest, comprising the following steps:
   i) recombinantly expressing the gonadotropin;
   ii) purifying the gonadotropin by subjecting a biological sample containing the gonadotropin at least to the steps of:
   a) reverse phase chromatography as a first chromatographic step,
   b) size exclusion chromatography, and
   c) hydrophobic interaction chromatography;
   wherein the steps are performed in the sequence of reverse phase chromatography, size exclusion chromatography, and hydrophobic interaction chromatography.

14. The manufacturing process according to claim 13, further comprising one or more of the following steps:
   (a) ion exchange chromatography;
   (b) anion exchanged chromatography;
   (c) affinity chromatography;
   (d) ultrafiltration;
   (e) diafiltration;
   (f) nanofiltration; and
   (g) virus inactivation.

15. The manufacturing process according to claim 13, wherein the gonadotropin is selected from the group consisting of FSH, CG, LH and TSH.

16. The process according to claim 2, wherein the organic solvent is isopropanol.

17. The process according to claim 10, wherein the gonadotropin is FSH.

18. The process according to claim 1, further comprising one or more steps selected from the group consisting of anion exchange chromatography, cation exchange chromatography, dye affinity chromatography, immune affinity chromatography, lectin affinity chromatography and perborate affinity chromatography.

19. The process according claim 1, additionally comprising a chromatofocusing step.

20. The process according to claim 1, wherein the process
   (i) does not comprise a buffer exchange step between the reverse phase chromatography and the size exclusion chromatography; and/or
   (ii) does not comprise a buffer exchange step between the size exclusion chromatography and the anion-exchange chromatography or the hydrophobic interaction chromatography; and/or
   (iii) does not comprise an immunoaffinity chromatography and/or a cation exchange chromatography;
   (iv) comprises only the three chromatographic steps reverse phase chromatography, size exclusion chromatography and hydrophobic interaction chromatography; or comprises only the four chromatographic steps reverse phase chromatography, size exclusion chromatography, anion exchange chromatography or chromatofocusing step, and hydrophobic interaction chromatography.

21. The process according to claim 1, wherein the biological sample is selected from the group consisting of cell culture medium, cell lysates, and natural source liquids.

22. The process according to claim 12, wherein the biological sample is selected from the group consisting of cell culture medium, cell lysates, and natural source liquids.

23. The process according to claim 13, wherein the biological sample is selected from the group consisting of cell culture medium, cell lysates, and natural source liquids.

* * * * *